(12) United States Patent
Dumont et al.

(10) Patent No.: US 11,854,295 B2
(45) Date of Patent: Dec. 26, 2023

(54) FINGERPRINT ACQUISITION DEVICE

(71) Applicant: IDEMIA IDENTITY & SECURITY FRANCE, Courbevoie (FR)

(72) Inventors: Denis Dumont, Courbevoie (FR); Sylvain Emile Henri Maillard, Courbevoie (FR)

(73) Assignee: IDEMIA IDENTITY & SECURITY FRANCE, Courbevoie (FR)

( * ) Notice: Subject to any disclaimer, the term of this patent is extended or adjusted under 35 U.S.C. 154(b) by 0 days.

(21) Appl. No.: 17/661,469

(22) Filed: Apr. 29, 2022

(65) Prior Publication Data

US 2022/0351536 A1 Nov. 3, 2022

(30) Foreign Application Priority Data

Apr. 30, 2021 (FR) .................................. 2104541

(51) Int. Cl.
*G06V 40/13* (2022.01)
*G06V 40/12* (2022.01)

(52) U.S. Cl.
CPC .......... *G06V 40/1318* (2022.01); *G06V 40/13* (2022.01); *G06V 40/1394* (2022.01)

(58) Field of Classification Search
CPC ............... G06V 40/1318; G06V 40/13; G06V 40/1394; G06V 40/1312; A61B 5/1172; G06F 21/32
See application file for complete search history.

(56) References Cited

U.S. PATENT DOCUMENTS

2020/0342200 A1* 10/2020 Furuta .................... H10K 59/12

FOREIGN PATENT DOCUMENTS

DE 202004012606 U1 12/2004
JP 2011-108128 A 6/2011

OTHER PUBLICATIONS

Preliminary Research Report received for French Application No. 2104541, dated Dec. 5, 2021, 5 pages (1 page of French Translation Cover Sheet and 4 pages of original document).
European Search Report and Search Opinion received for EP Application No. 22170166.7, dated Sep. 6, 2022, 18 pages (9 pages of English Translation and 9 pages of Original Document).
Office Action received for European Application No. 22170166.7, dated Jul. 14, 2023, 12 pages (6 pages of English Translation and 6 pages of Original Document).

* cited by examiner

*Primary Examiner* — John B Strege
(74) *Attorney, Agent, or Firm* — WOMBLE BOND DICKINSON (US) LLP

(57) ABSTRACT

A fingerprint acquisition device comprising, a space for receiving a finger of a user, a light source configured to emit a illumination light illuminating the space, a camera configured to acquire an image of a fingerprint of the finger, when the finger is received in the space, and, a polarization system configured to polarize the illumination light before the illumination light reaches the space and after the illumination light has passed through the space, and to polarize an ambient light emanating from outside the device and propagating towards the camera, before the ambient light reaches the space, and to polarize the ambient light after the ambient light has passed through the space.

8 Claims, 6 Drawing Sheets

FINGERPRINT ACQUISITION DEVICE

CROSS-REFERENCE TO RELATED APPLICATIONS

This application claims priority pursuant to 35 U.S.C. 119(a) to France Patent Application No. 2104541, filed Apr. 30, 2021, which application is incorporated herein by reference in its entirety.

TECHNICAL FIELD OF THE INVENTION

The present invention relates to a fingerprint acquisition device.

STATE OF THE ART

A known fingerprint acquisition device comprises a camera which acquires an image of a fingerprint when a user has placed a finger in an acquisition space in view of the camera, located above a translucent wall. To improve the dynamics of the image, the finger is lit by generally brief, strong lighting generated by a light source internal to the device, and passing through the translucent wall.

However, this lighting is likely to dazzle the user who is seeking to place their finger correctly in the acquisition space. Furthermore, an ambient lighting generated by the environment outside the device may pass through the translucent wall and reach the camera, which might disrupt the acquisition.

In order to overcome these problems, it has been proposed to include in the device an opaque wall opposite the first acquisition wall, so that the acquisition space is provided between the translucent wall and the opaque wall. In use, the opaque wall is located above the first translucent wall; in other words, the user places their finger or more generally their hand under the opaque wall so that the fingerprint of said finger can be imaged by the camera.

The opaque wall prevents the user from being dazzled by the internal light source of the device and protects the camera from ambient lighting that interferes with its operation.

However, the opaque wall prevents the user from seeing where their hand is passing. The acquisition space is concealed, which puts off some users who hold their hands back. The impact on the performance of the device thus is very negative for some of these users.

SUMMARY OF THE INVENTION

One aim of the invention is to acquire a fingerprint by means of a reliable device, while being comfortable to use.

For this purpose, a fingerprint acquisition device is proposed, the device comprising:
- a space for receiving a finger of a user,
- a light source configured to emit a illumination light illuminating the space,
- a camera configured to acquire an image of a fingerprint of the finger, when the finger is received in the space, the device being characterized in that it comprises a polarization system configured to:
  polarize the illumination light in a first direction before the illumination light reaches the space,
  polarize the illumination light in a second direction after the illumination light has passed through the space, the second direction being different from the first direction,
  polarize in the second direction an ambient light emanating from outside the device and propagating towards the camera, before the ambient light reaches the space, and
  polarize the ambient light in a third direction after the ambient light has passed through the space, the third direction being different from the second direction.

By virtue of the polarization system, the power of the ambient light is greatly reduced before reaching the camera, due to the fact that said light undergoes two successive polarizations in two different polarization directions (the first direction and the second direction). As a consequence, the ambient light does not dazzle the camera, and does not disrupt its operation. Additionally, the user can observe the space through the polarization system, which allows them to correctly position their finger, with a view to ensuring correct acquisition of their fingerprint by the camera. Furthermore, the polarization system has the advantage of contributing to improving the dynamics of the image showing the fingerprint acquired by the camera. The operation of the device is thus made more reliable.

The same phenomenon of power reduction applies to the illumination light emitted by the light source of the device, since it also undergoes two polarizations in two different directions (the second direction and the third direction) by virtue of the polarization system. As a consequence, a user looking at the space in which their finger is received through the second polarizer is not dazzled by this illumination light. Thus, the device is more comfortable to use.

The fingerprint acquisition device may also comprise the following optional features, taken either alone or in combination every time this makes technical sense:

The second direction may be perpendicular to the first direction.

The third direction and the first direction may be identical.

The polarization system may comprise a first polarizer configured to:
  polarize the illumination light in the first direction before the illumination light reaches the space, and
  polarize the ambient light in the first direction after the ambient light has passed through the space.

The first polarizer can delimit the space, so that the illumination light reaches the space upon exiting the first polarizer.

The device may comprise a housing defining a cavity containing the light source, and a transparent wall forming a window between the cavity and the space for receiving the finger, and the first polarizer may be attached to the transparent wall.

The device may comprise a housing defining a cavity containing the light source, and a transparent wall forming a window between the cavity and the space for receiving the finger, the first polarizer being arranged in the housing.

The device may comprise a housing defining a cavity containing the light source, the first polarizer forming a transparent window separating the cavity and the space for receiving the finger.

The polarization system may comprise a second polarizer configured to:
  polarize the illumination light in the second direction after the illumination light has passed through the space, and
  polarize the ambient light in the second direction before the ambient light reaches the space.

The second polarizer may delimit the space, so that the ambient light reaches the space upon exiting the second polarizer.

The first polarizer and the second polarizer may extend parallel to one another.

The device may comprise a translucent wall, the second polarizer being attached to the translucent wall.

The device may define a front access to the space and two side accesses to the space which are opposite one another with respect to the front access, so as to allow the user to move the finger following a straight path, inserting the finger into the space by one of the two side accesses, and removing the finger from the space by the other side access.

The device may comprise a housing defining a cavity containing the light source, and a transparent wall forming a window between the cavity and the space for receiving the finger, the camera being configured to acquire the image of the fingerprint of the finger, when the finger is placed on the transparent wall.

BRIEF DESCRIPTION OF THE FIGURES

Other characteristics, purposes and advantages of the invention will become clear from the following description, which is purely illustrative and non-limiting, and which must be read in the context of the attached drawings in which.

In the set of figures, similar elements are marked with identical references.

DETAILED DESCRIPTION OF THE INVENTION

Figure 1:
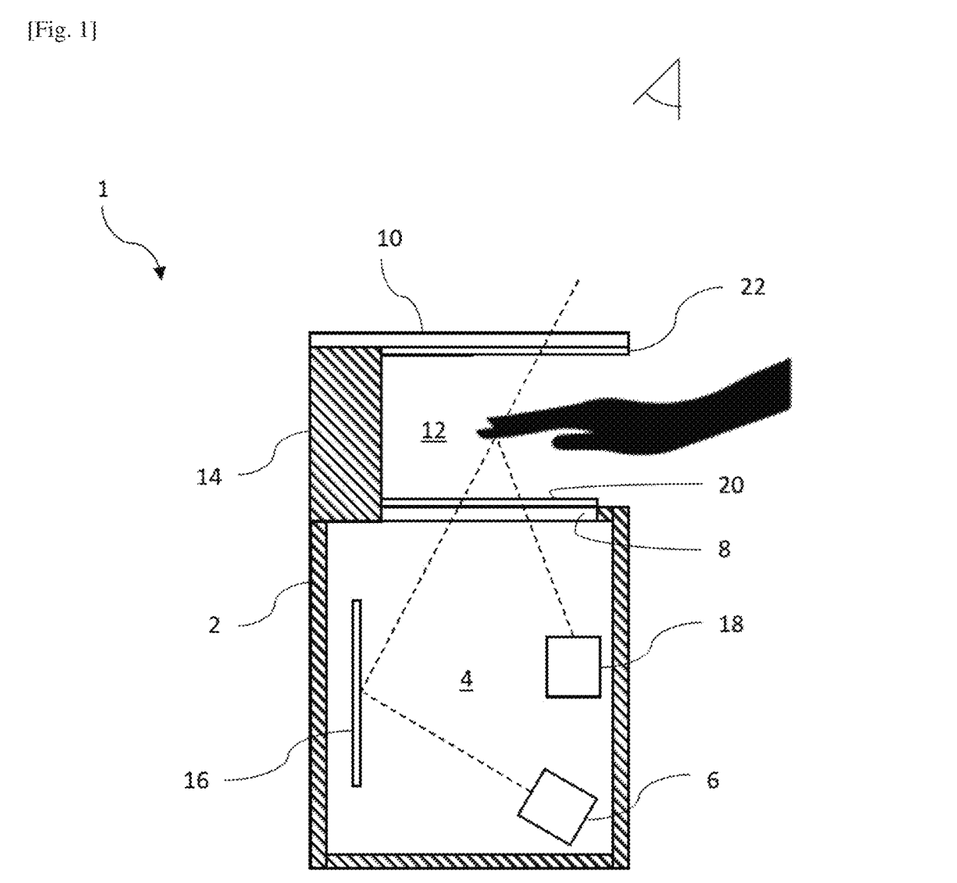
FIG. 1 is a schematic cross sectional view of a fingerprint acquisition device according to a first embodiment of the invention.

In reference to FIG. 1, a fingerprint acquisition device 1 comprises a housing 2 defining an internal cavity 4.

The fingerprint acquisition device 1 further comprises a light source 6. The light source 6 is arranged in the internal cavity 4.

The light source 6 is configured to emit a light in the visible domain and/or in a non-visible domain (for example infrared).

By convention, the light emitted by the light source 6 is referred to in this text as "illumination light", and, by contrast, a light emitted by a source external to the fingerprint acquisition device is referred to as "ambient light".

In the present disclosure, an element qualified as "translucent" should be interpreted as any medium through which light can pass, in other words a non-opaque material, without any additional conditions (unless such conditions are explicitly indicated).

Furthermore, an element qualified as "transparent" in the present disclosure should be interpreted as a medium that is not only translucent but which also allows visibility to pass through it. In other words, it is possible to see an object clearly through a transparent element, while this is not necessarily the case through a translucent element.

The fingerprint acquisition device 1 comprises a transparent wall 8.

The transparent wall 8 forms a part of a wall of the housing 2, typically an upper wall when the device 1 is in a use position. The transparent wall 8 constitutes a window between the internal cavity 4 and the outside of the housing 2. The transparent wall 8 has an inner surface in the internal cavity 4, and an outer surface outside the housing 2, opposite the inner surface. Preferably, the illumination light can only exit the housing 2 through the transparent wall 8.

The inner and outer surfaces of the transparent wall 8 are, for example, planar.

The transparent wall 8 is preferably transparent and/or homogeneous and/or isotropic. For example, the transparent wall 8 is made of glass.

The fingerprint acquisition device 1 further comprises a translucent wall 10, arranged opposite and separated from the transparent wall 8 so as to arrange therebetween a space 12 in which a user can place at least one of their fingers.

For example, the height of the arranged space 12, measured as the distance separating the transparent wall 8 and the translucent wall 10, is comprised between 3 centimeters and 15 centimeters.

The transparent wall 8 extends between the internal cavity 4 and the space 12.

The translucent wall 10 has an inner surface oriented towards the space 12, and an outer surface opposite the inner surface. The outer surface opens onto the outside of the fingerprint acquisition device 1, in the sense that it is visible to a user, in particular to a user placing at least one of their fingers in the space 12.

The inner and outer surfaces of the translucent wall 10 are, for example, planar.

The translucent wall 10 is preferably transparent and/or homogeneous and/or isotropic, but this is not mandatory. For example, the translucent wall 10 is made of polymethyl methacrylate (plexiglass).

The fingerprint acquisition device 1 further comprises a connecting part 14 which connects the translucent wall 10 to the transparent wall 8, acting as a spacer to keep the two walls 10, 12 separated from one another. This connecting part 14 can be part of the housing 2 or be an element attached to the housing 2. The translucent wall 10 extends in a cantilevered fashion from this connecting part 14, facing the transparent wall 8. The translucent wall 10 thus forms a cap.

Figure 2:
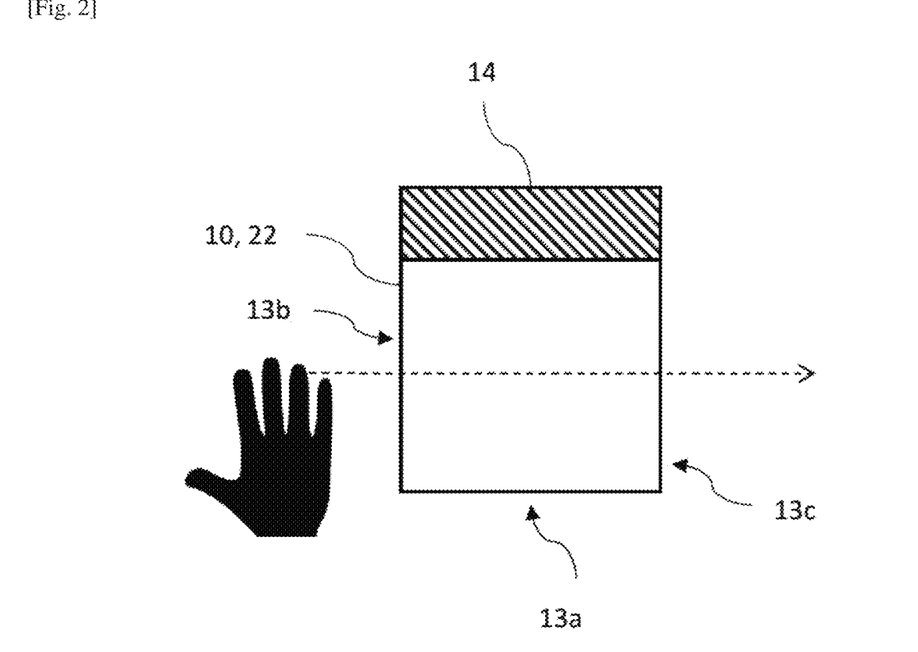
FIG. 2 is a top view of the fingerprint acquisition device according to the first embodiment of the invention.

In reference to FIG. 2, the connecting part 14 is arranged to provide a front access 13a to the space 12 (which is located in FIG. 1 to the right of the space 12 as it is) as well as two side accesses 13b, 13c to this space 12, which are opposite one another with respect to the front access 13a. In other words, the space 12 is located between the two side accesses 13b, 13c, and is further located between the front access 13a and the connecting part 14. A user can thus insert a finger into the space 12 via the front access 13a or via one of the side accesses 13b, 13c.

The fingerprint acquisition device 1 is configured so that the illumination light emitted by the light source 6 can pass through the transparent wall 8 (thus exiting the housing 2), then pass through the space 12 arranged between the two translucent walls 8, 10, and then pass through the translucent wall 10. The device 1 can in particular comprise an optical system 16 configured to guide the light emitted by the light source 6 towards the transparent wall 8. In the embodiment shown in FIG. 1, the optical system 16 is formed by a mirror, but the optical system can be more complex and can, alternatively, be absent if the light source 6 faces the transparent wall 8.

The fingerprint acquisition device 1 further comprises a camera 18 configured to acquire images showing the fingerprint of a finger placed in the space 12. In the present text, the term "camera" is not limited to a means for acquiring images in video form; it should be interpreted in a broad sense, as covering any image acquisition means, including in the form of a video or single image.

The camera 18 is arranged in the internal cavity 4 of the housing 2, so as to be able to receive light emanating from the space 12. The camera 12 is in particular configured to acquire an image of a finger received in the space 12.

The camera 18 is in particular configured to perform such an acquisition when the finger is suspended in the space 12, without it touching the device 1. This is advantageous with respect to fingerprint acquisition devices that require a finger to be placed in contact on an acquisition surface, since such a contact is likely to deform the fingerprint, which can lead to an imperfect acquisition of this fingerprint.

The device 1 may comprise an optical system (not shown) to redirect the light emanating from the space 12 towards the camera 18.

The camera 18 is capable of communicating with an image-processing unit configured to implement all or part of an authentication process that is known in the prior art. For example, this authentication process can have the aim of identifying the user that has placed their finger in the space 12, or of determining whether or not this user is authorized to access a service or a zone.

It should be noted that this image-processing unit can be comprised in the fingerprint acquisition device 1, although this is not a requirement since the unit can be located outside of this device 1. In the second case, the fingerprint acquisition device 1 can comprise a communication interface to communicate with an external device, such as a server, provided with such an image-processing unit.

The fingerprint acquisition device 1 further comprises a polarization system. Typically, the polarization system is configured to
polarize the illumination light in a first direction before the illumination light reaches the space 12,
polarize the illumination light in a second direction after the illumination light has passed through the space 12, the second direction being different from the first direction,
polarize in the second direction an ambient light emanating from outside the device 1 and propagating towards the camera 18, before the ambient light reaches the space 12, and
polarize the ambient light in a third direction after the ambient light has passed through the space 12, the third direction being different from the second direction.

In the first embodiment shown in FIG. 1, the polarization system comprises a first polarizer 20 configured to polarize a light in a first direction.

The first polarizer 20 is transparent. The first polarizer is arranged so that the illumination light emitted by the light source 6 passes through same, before the illumination light reaches the space 12.

The first polarizer 20 is further arranged so that the ambient light emitted by a source external to the device 1 passes through same, before this ambient light reaches the camera 18. Thus, in this embodiment, the first direction and the third direction are identical.

In the first embodiment shown in FIG. 1, the first polarizer 20 delimits the space 12, so that the illumination light originating from the light source 6 reaches the space 12 upon exiting the first polarizer 20. This makes it possible to guarantee that the first polarizer 20 is the last optical element of the device that modifies the properties of the light emanating from the light source 6 before this light reaches the space 12. If optical elements of the device such as the transparent wall 8 are located downstream of the first polarizer 20, they can alter the polarization of the illumination light, so that the illumination light would no longer be perfectly in the first polarization direction when it reaches the space 12. This problem is avoided in this first embodiment.

In practice, the first polarizer 20 is placed outside the housing 2, between the transparent wall 8 is the space 12.

The first polarizer 20 is attached to the transparent wall 8. More precisely, the first polarizer 20 is attached to the outer surface of the transparent wall 8.

The first polarizer 20 is presented for example in the form of a film attached to the transparent wall 8 by means of an adhesive.

In the first embodiment shown in FIG. 1, the polarization system further comprises a second polarizer 22. The first polarizer 20 is configured to polarize the light in a second direction different from the first polarization, after the light has passed through the space 12. The space 12 is located between the first polarizer 20 and the second polarizer 22.

The second polarizer is translucent, or even transparent.

The second polarizer 22 delimits the space 12, so that the ambient light reaches the space 12 upon exiting the second polarizer 22. This makes it possible to guarantee that the second polarizer 22 is the last optical element of the device that modifies the properties of the ambient light emanating from outside the device 1, before it enters the lighting space 12.

In practice, the second polarizer 22 is attached to the translucent wall 10. More precisely, the second polarizer 22 is attached to the inner surface of the translucent wall 10. In this way, the translucent wall 10 protects the second polarizer 22 from aggressions external to the device 1, which would risk damaging it and thus altering the polarization function thereof.

The second polarizer 22 is presented for example in the form of a film attached to the translucent wall 10 by means of an adhesive.

The first polarizer 20 and the second polarizer 22 extend parallel to one another.

As shown previously, the second polarization direction is different from the first polarization direction. Preferentially, the angle between the first polarization direction and the second polarization direction is comprised between 70 and 110 degrees, or is comprised between 80 and 100 degrees. Even more preferentially, the second polarization direction is perpendicular to the first polarization direction.

A method of acquiring fingerprints using the fingerprint acquisition device 1 comprises the following steps.

It is presumed that the fingerprint acquisition device 1 is placed in a use position, wherein the transparent wall 8 forms an upper wall portion of the housing 2 and wherein the translucent wall 10 is located above the transparent wall 8.

A user positions themself in front of the device 1, and in particular facing the front access 13a to the space 12. The device 1 is typically placed at a height that allows the user to overlook the device 1, so that the second polarizer 20 is located between the space 12 and the eyes of the user.

The user inserts at least one of their fingers into the space 12 arranged between the polarizers 20 and 22, so that the fingerprint of one finger is in view of the camera 18.

The user may in particular insert a finger by one of the side accesses to the space 12, for example the side access 13b, and move it towards the other side access 13c following a straight path as shown in FIG. 2.

The light source 6 emits the illumination light discussed previously, in order to illuminate the space 12 and in particular the finger that the user has placed therein. The emission of the illumination light is for example triggered upon detecting the presence of the finger in the field of vision of the camera 18, by means of adequate detection means of the fingerprint acquisition device 1.

The illumination light is typically emitted in the form of a series of brief, strong flashes.

The illumination light propagates in the internal cavity 4, is redirected towards the transparent wall 8 by the optical system 16, and passes through the transparent wall 8. The illumination light furthermore passes through the first polarizer 20, which polarizes the illumination light in the first direction. The first polarizer 20 acts on the illumination light as a filter: every polarization direction that may be present in the illumination light upstream of the first polarizer 20 is eliminated when this light passes through the first polarizer 20, with the exception of the first direction.

Once polarized in the first direction by the first polarizer 20, the illumination light propagates in the space 12.

A part of the illumination light polarized in the first direction illuminates in particular the fingerprint of the finger placed in the space 12. This part of the illumination light is reflected by the finger of the user, and penetrates once again into the housing 2 passing through the first polarizer 20 and the transparent wall 8, before reaching the camera 18.

The camera 18 acquires an image showing the fingerprint of the finger received in the space 12. This image can then be used in the context of the above-mentioned authentication process.

During this acquisition, it is not necessary for the finger to be placed in contact with the device 1, in particular with the transparent wall 8 or the first polarizer 20.

Since the user can see the space 12 through the translucent wall 10 and through the second polarizer 22, the user can very easily position their finger in the space 12 facing the camera 18, and this makes it possible to shorten the time it takes to carry out the process. Conversely, a user who cannot see where their finger is with respect to the transparent wall 8 would tend to hesitate or at least fumble to place their finger correctly, which would only delay the triggering of the acquisition step or lead to obtaining an image that does not show the fingerprint correctly, thus compromising the proper functioning of the process that then uses this image.

Of course, the use of the light source 6 improves the readability of the fingerprint in the image acquired by the camera 18. The first polarizer 20 further improves the dynamics of this image.

It has been seen previously that a portion of the illumination light polarized in the first direction has been reflected by the finger. A remaining part of the illumination light polarized in the first direction, not blocked by the finger or any other possible obstacle, passes entirely through the space 12 towards the second polarizer 22 and the translucent wall 10, and then passes through the second polarizer 22. This remaining part then undergoes a new polarization, but this time in the second direction, different from the first direction. Thus, the second polarizer applies to the remaining part of the illumination light a second filtering eliminating a large part of the power transported by this light. As a consequence, the user looking towards the space 12 through the second polarizer 22 is not dazzled by the illumination light.

Figure 3:
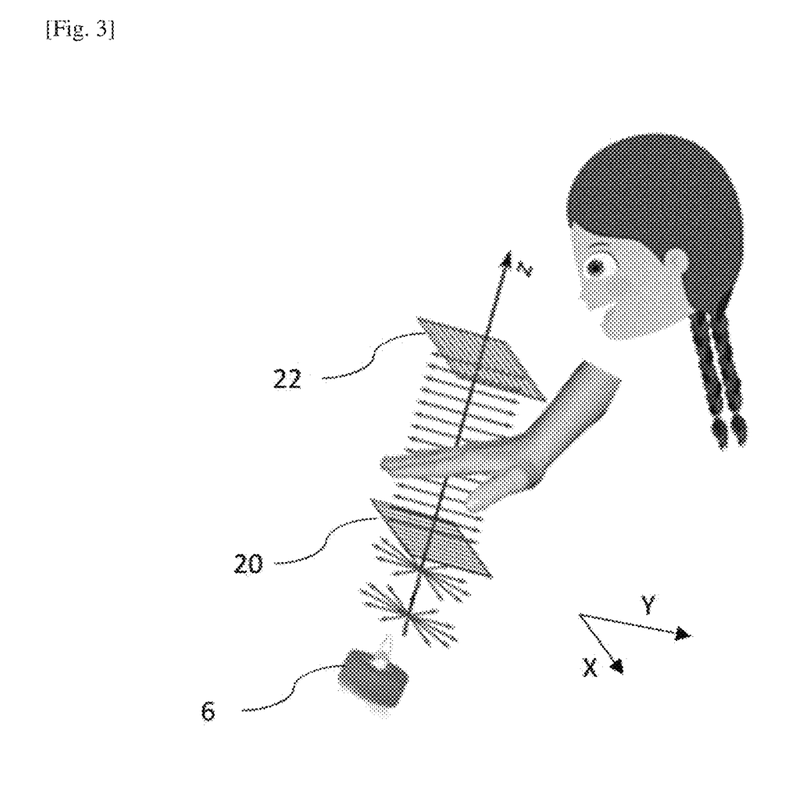
FIG. 3 shows a double polarization applied to a illumination light, when the latter passes through two polarizers.

FIG. 3 schematically shows an example of double polarization of the illumination light performed by the two polarizers 20 and 22. In this example, the first polarizer 20 polarizes the illumination light in a direction parallel to an axis X, and the second polarizer polarizes the illumination light in a direction parallel to an axis Y perpendicular to the axis X. In this situation of perpendicularity, the illumination light is completely eliminated by the two polarizers 20, 22 before reaching the user.

Now we will consider an ambient light emitted by a source external to the fingerprint acquisition device 1. Part of this ambient light can pass through the translucent wall 10 and the second polarizer 22, and then pass through the space 12, pass through the transparent wall 8 and the first polarizer (supposing that it is not blocked by a finger or any other obstacle placed in the space 12). This part of the ambient light then undergoes two successive polarizations before reaching the camera 18: a polarization in the second direction, and then a polarization in the first direction. In this way, a large part of the power of the ambient light is eliminated before reaching the camera 18, which has the consequence of limiting or even eliminating the disruptions that the ambient light would cause to the image acquisition performed by the camera 18.

Figure 4:
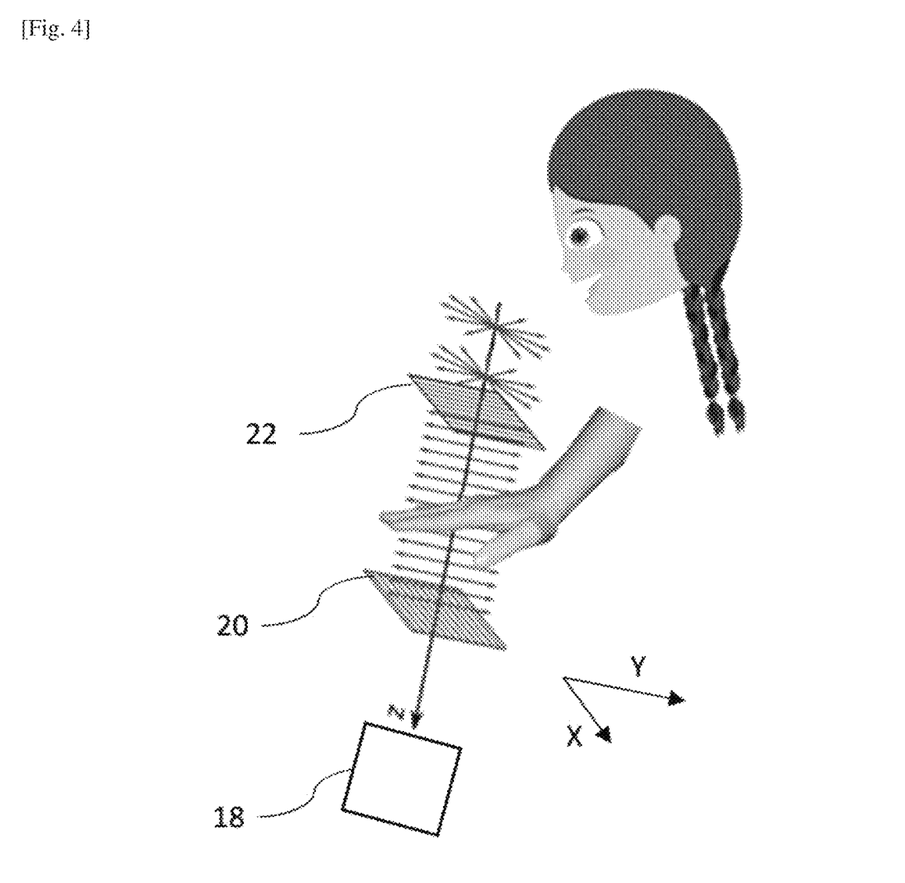
FIG. 4 shows a double polarization applied to an ambient light, when the latter passes through two polarizers.

FIG. 4 schematically shows the double polarization of the ambient light by the two polarizers 20 and 22 in the same example of embodiment as that of FIG. 3. In this example, the ambient light is completely eliminated by the two polarizers 20, 22 before reaching the camera 6.

The ambient light additionally allows the user looking towards the upper surface of the translucent wall 10 to look at the space 12 where they have placed their finger.

Ultimately, the two polarizers 20, 22 make it possible to achieve a double objective: to reduce the risks of dazzling a user seeking to position their finger correctly with a view to the device 1 acquiring their fingerprint, and to reduce the risks of dazzling the camera 18. In the particular case in which the first polarization direction and the second polarization direction are perpendicular, the user and the camera 18 both see the finger received in the space, but do not see each other, which is highly advantageous since the above-mentioned dazzling risks are entirely eliminated.

In the above, we have taken the example of the acquisition of the image of a user's finger. However, the device 1 can obviously be used to acquire one or more fingerprint images of several fingers of the user. For this, the user can insert several of their fingers into the space 12, so that the fingers pass together through the space 12 going from one side access to the other, following a straight path, as shown by a dotted arrow in FIG. 2. During this passing movement, the fingers are successively or simultaneously in the view of the camera 18, so that one or more images showing them can be acquired by the camera 18.

Figure 5:
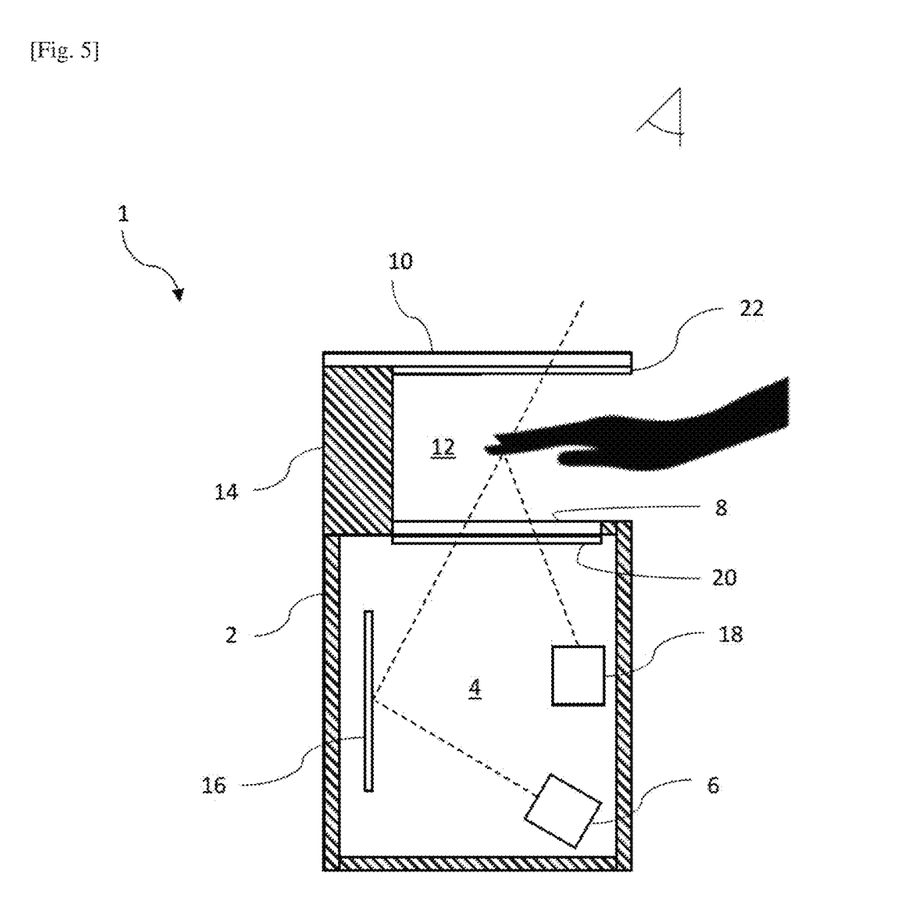
FIG. 5 is a schematic cross sectional view of a fingerprint acquisition device according to a second embodiment of the invention.

FIG. 5 shows a second embodiment of the device 1, which differs from the first embodiment shown in FIG. 1 in the form of its polarization system: indeed, the first polarizer 20 is located in the internal cavity 4 of the housing 2. This makes it possible to protect the first polarizer 20 against aggressions from outside the housing 2. For example, the first polarizer 20 is attached to the inner surface of the transparent wall 8. As a counterpart to this protective effect, the filtering of light by the two polarizers 20 and 22 may be slightly less efficient than in the first embodiment, because the first translucent wall may "depolarize" the illumination light that was polarized in the first direction, before its entry into the space 12 and its subsequent polarization by the second polarizer 22.

In the two embodiments described previously, the polarization system only comprises two polarizers. In particular, the first polarizer 20 not only polarizes the light emanating from the light source 6, but also the light going to the camera 6. This configuration has the advantage of being simple to manufacture.

Figure 6:
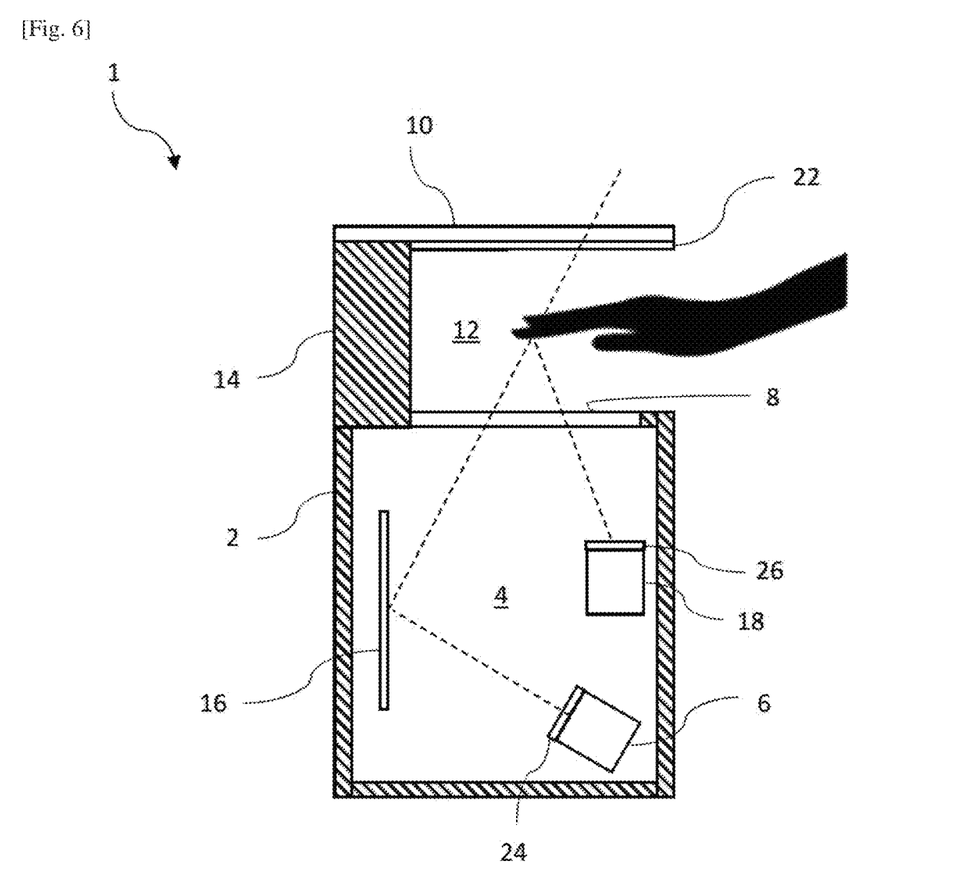
FIG. 6 is a schematic cross sectional view of a fingerprint acquisition device according to a third embodiment of the invention.

FIG. 6 shows a third embodiment of the device 1, which differs from the second embodiment in that the polarization system comprises three polarizers. More precisely, the first polarizer 20 of the second embodiment is replaced in the third embodiment by a pair of separate polarizers 24, 26.

On the one hand, the polarizer 24 is configured to polarize in the first direction the light emanating from the light source 6 before it reaches the space 12. The polarizer 24 is arranged in the internal cavity 4. The polarizer 24 is attached for example to the light source 6, but can alternatively be separated from same. The polarizer 24 is translucent, or even transparent.

Furthermore, the polarizer 26 is configured to polarize the light coming from the space 4 in a third direction, before said light reaches the camera. The polarizer 26 is also arranged in the internal cavity 4. The polarizer 26 is attached for example to the camera 18, but can alternatively be separated from same. The polarizer 26 is transparent.

The third direction is preferably identical to the first direction, in order to optimize the attenuating performance of the polarization system, but not necessarily.

One advantage of the third embodiment is that the pair of polarizers 24, 26 can have small dimensions. Thus, the cost of the pair of polarizers 24, 26 may be less than the cost of the polarizer 20.

Other embodiments of the fingerprint acquisition device 1 not shown can also be envisaged. These embodiments can comprise the features described hereunder.

The first polarizer 20 may be positioned in the housing 2, separated from the transparent wall 8.

The second polarizer 22 may furthermore be attached to the outer surface of the translucent wall 10, or separated from the translucent wall 10.

It is not at all compulsory for the two polarizers to be aligned, as long as the illumination light emitted by the light source 6 can pass through them successively, and ambient light emanating from the outside can pass through them successively, before this light can reach the camera 18.

In the embodiments shown in FIGS. 1 and 5, the polarizers 20, 22 and the two translucent walls 8, 10 constitute four translucent elements through which the illumination light successively passes, and through which an ambient light emanating from outside the device 1 can successively pass. However, it is understood that the device 1 can perfectly well only comprise two translucent elements providing the above-mentioned polarization functions and furthermore delimiting therebetween the space 12 in which the fingers of users are received.

In the foregoing, it has also been supposed that the device 1 is of the contactless type, in the sense that it is not specially required for a finger to be placed in contact with the device 1 during the acquisition. However, the device 1 may alternatively be of the type with contact.

What is claimed is:

1. A contactless fingerprint acquisition device comprising:
    a housing defining a cavity,
    a space for receiving a finger of a user,
    a transparent wall forming a window between the cavity and the space for receiving the finger,
    a translucent wall arranged opposite and separated from the transparent wall so as to arrange therebetween the space for receiving the finger of the user,
    a light source configured to emit a illumination light illuminating the space, wherein the light source is contained in the housing,
    a camera configured to acquire an image of a fingerprint of the finger, when the finger is received in the space without contacting the contactless fingerprint acquisition device,
    a polarization system comprising:
    a first polarizer which forms the transparent wall or is attached to the transparent wall, the first first polarizer configured to:
        polarize the illumination light in a first direction before the illumination light reaches the space, and
        polarize the ambient light in the first direction emanating from outside the device and propagating towards the camera after the ambient light has passed through the space and before the ambient light reaches the camera, and
    a second polarizer which is attached to the translucent wall and extends parallel to the first polarizer, the second polarize being configured to: polarize the illumination light in a second direction after the illumination light has passed through the space, and polarize the ambient light in the second direction before the ambient light reaches the space, wherein the second direction is different from the first direction.

2. The device according to claim 1, wherein the second direction is perpendicular to the first direction.

3. The device according to claim 1, wherein the third direction and the first direction are identical.

4. The device according to claim 1, wherein the first polarizer delimits the space, so that the illumination light reaches the space upon exiting the first polarizer.

5. The device according to claim 1, wherein the first polarizer is arranged in the housing.

6. The device according to claim 1, wherein the second polarizer delimits the space, so that the ambient light reaches the space upon exiting the second polarizer.

7. The device according to claim 1, further defining a front access to the space and two side accesses to the space which are opposite one another with respect to the front access, so as to allow the user to move the finger following a straight path, inserting the finger into the space by one of the two side accesses, and removing the finger from the space by the other side access.

8. The device according to claim 1, wherein the camera is configured to acquire the image of the fingerprint of the finger, when the finger is placed on the transparent wall.

* * * * *